United States Patent [19]

Cook et al.

[11] Patent Number: 5,504,114

[45] Date of Patent: Apr. 2, 1996

[54] METHOD FOR CONTROLLING BIRD POPULATIONS

[75] Inventors: Mark E. Cook; Michael W. Pariza; Kisun N. Lee; Bernard C. Wentworth, all of Madison, Wis.

[73] Assignee: Wisconsin Alumni Research Foundation, Madison, Wis.

[21] Appl. No.: 297,471

[22] Filed: Aug. 29, 1994

Related U.S. Application Data

[63] Continuation-in-part of Ser. No. 875,896, Apr. 29, 1992, Pat. No. 5,430,066, and a continuation-in-part of Ser. No. 7,413, Jan. 22, 1993, Pat. No. 5,428,072.

[51] Int. Cl.$^6$ .................................................. A61K 31/20
[52] U.S. Cl. ............................................. 514/558; 514/560
[58] Field of Search ................................. 514/558, 560

[56] References Cited

U.S. PATENT DOCUMENTS

| | | | |
|---|---|---|---|
| 4,603,142 | 7/1986 | Burger et al. | 514/456 |
| 4,868,001 | 9/1989 | Maruta | 426/623 |
| 5,017,614 | 5/1991 | Pariza et al. | 514/558 |
| 5,045,338 | 9/1991 | Klemann et al. | 426/611 |
| 5,070,104 | 12/1991 | Pariza et al. | 514/549 |
| 5,162,337 | 11/1992 | Elbrecht et al. | 514/300 |

FOREIGN PATENT DOCUMENTS 294982 of 1986 Japan.

OTHER PUBLICATIONS

Y. L. Ha; N. K. Grimm and M. W. Pariza, *Carcinogenesis*, vol. 8, No. 12, pp. 1881–1887 (1987).
Y. L. Ha; N. K. Grimm and M. W. Pariza, J. Agric. Food Chem., vol. 37, No. 1, pp. 75–81 (1987).
M. W. Pariza, Food Research Institute 1988 Annual Fall Meeting, Oct. 12, 1988.
The Merck Index, Tenth Edition (1983), p. 790.
The Marck Veterinary Manual, Fifth Edition (1979), pp. 1340–1343 and 1374 to 1379.

*Primary Examiner*—Raymond Henley, III
*Assistant Examiner*—Kevin E. Weddington
*Attorney, Agent, or Firm*—Quarles & Brady

[57] ABSTRACT

A method of controlling a bird population in an area comprises administering to the female birds in the area an amount of a conjugated linoleic acid (CLA) which is effective to prevent their eggs from hatching. Baits containing the conjugated linoleic acid also are disclosed.

10 Claims, No Drawings

METHOD FOR CONTROLLING BIRD POPULATIONS

The present application is a continuation-in-part of co-pending applications U.S. Ser. No. 07/875,896, filed Apr. 29, 1992, now U.S. Pat. No. 5,430,066, and U.S. Ser. No. 08/007,413, filed Jan. 22, 1993, now U.S. Pat. No. 5,428,072.

FIELD OF THE INVENTION

The present invention generally relates to controlling bird populations. More particularly, it relates to a method of controlling the reproductivity of birds and baits for use in the method.

BACKGROUND OF THE INVENTION

There are areas in which the size of the local bird populations can present problems. At airports, the presence of a large bird population, especially seagulls, can present safety problems because it increases the likelihood that a bird(s) will be sucked into a jet engine and cause engine failure. At cattle feed lots, where bird populations can reach three million or more per day, the birds can cause multiple problems, such as feed consumption, defecation and the spreading of diseases, such as salmonella. In addition, large populations of birds such as pigeons, starlings, crows, red wing blackbirds and house sparrows can cause problems in parks, cities and neighborhoods.

Varied approaches have been tried in the past to control such populations. Obviously, the drugging or poisoning of the birds is not acceptable because of the risk to other animals, including humans, and the accumulation of dead birds. Attempts have been made to drive the birds away with noise or light or other means. However, none of these approaches have been particularly successful.

Therefore a need exists for a method of controlling bird populations, especially in areas where they are pests.

There also is a need for a safe and effective method of controlling the reproductivity of birds without harming the birds or endangering other animals, including humans. Bird populations can be controlled more effectively if they are allowed to mate, lay eggs and occupy part of their life cycle in an attempt to hatch eggs.

BRIEF SUMMARY OF THE INVENTION

It is an object of the present invention to disclose a safe and effective method of controlling bird populations.

It also is an object of the present invention to disclose a safe, effective and reversible method of controlling the reproductivity of birds without harming the birds or endangering other animals.

We have discovered a safe and effective method of controlling bird populations in an area by reversibly controlling the reproductivity of the birds by administering to female birds a safe amount of conjugated linoleic acid selected from 9,11-octadecadienoic acid; 10,12-octadecadienoic acid; mixtures thereof and non-toxic salts thereof (CLA), in an amount which is effective to prevent the eggs of the female birds from hatching.

We also have discovered that the conjugated linoleic acid can be readily administered to the birds by incorporating it in a bait which is tailored for the targeted species of birds by making the bait of a particle size preferred by those birds and/or by adding to the bait a substance which attracts the targeted species of bird.

The present invention provides a safe and effective way of controlling bird populations in areas where such control is desired. Since the conjugated linoleic acids are nontoxic to the birds and other animals, including humans, it can be safely used where toxic chemicals cannot.

It will be apparent to those skilled in the art that the forementioned objects and other advantages may be achieved by the practice of the present invention.

DESCRIPTION OF THE PREFERRED EMBODIMENT

In a preferred embodiment of the method of the present invention, a conjugated linoleic acid, which is selected from 9,11-octadecadienoic acid; 10,12-octadecadienoic acid; mixtures thereof and non-toxic salts thereof (CLA), is administered to a targeted species of bird by feeding to them a bait which contains an amount of the CLA which when the bait is consumed in normal amounts by a targeted species of female bird will prevent the eggs of the bird from hatching.

The amount of the conjugated linoleic acid to be added to the bait will vary with the species, size, and eating habits of the targeted birds. For most species the bait will contain about 0.1% to about 1% of CLA based on the total weight of the bait. Normally the administration of the CLA in amounts ranging from 0.1 gram to 1 gram per kilogram of body weight of a bird causes the eggs laid by the female birds not to hatch. However, since the conjugated linoleic acids are natural food ingredients and relatively non-toxic, the amount which can be administered is not critical as long as it is enough to be effective.

The bait may, in addition to the CLA, contain a substance that is attractive to the bird and it will be of a particle size and/or shape preferred by the targeted species of bird. For example, an ideal bait for seagulls is artificial fish smelt (about 12 to 16 cm×2 to 3 cm) which can be made by extruding chicken egg components which contain CLA from the yolk and an albumin coat; the same type of bait could be used to control waterfowl populations, e.g. Canadian geese, Mallard ducks and swans. For pigeons an ideal bait would be unpopped popcorn (about 0.5 cm×0.5 cm) in which a core has been removed from the kernel and the space filled with CLA; very few other birds eat this type of food during breeding season. For blackbirds and starlings a good bait would be extruded chicken eggs containing CLA in a particle size of about 2.5 cm×1 cm. In contrast, a good bait for crows would be the same sort of extruded egg product having a particle size of about 6 cm×1.5 cm. A good bait for house sparrows would be crumbled particles (about 0.4 cm to 0.4 cm) of turkey pellets containing CLA.

An important advantage of the method of the present invention is that the CLA has no other effect upon the bird and if the bird leaves the area to be controlled and does not continue to consume the CLA-containing feed, it will once again be able to lay eggs that can be hatched. Furthermore, because the CLA only affects the hatching of the eggs, the use of the CLA-containing bait can generally be restricted to use during the nesting season for the targeted species of bird.

The ability of CLA to prevent the hatching of eggs does not appear to be restricted to any specific species of birds. Therefore, for best results it is preferred to use a bait of a particle size preferred by the targeted birds in the areas where they normally feed and to include in the bait, when possible, a substance which is attractive primarily to the targeted species. For example, if the targeted species is a meat-eating bird the bait might contain meat.

The practice of the present invention is further illustrated by the examples which follow:

EXAMPLE 1

Synthesis of Conjugated Linoleic Acids From Linoleic Acid and Safflower Oil

Ethylene glycol (1000 g) and 500 g potassium hydroxide (KOH) are put into a 4-neck round bottom flask (5000 ml). The flask is equipped with a mechanical stirrer, a thermometer, a reflux condenser, and a nitrogen inlet. (The nitrogen introduced in first run through two oxygen traps).

Nitrogen is bubbled into the ethylene glycol and KOH mixture for 20 min and the temperature is then raised to 180° C.

1000 g of linoleic acid, corn oil or safflower oil is then introduced into the flask. The mixture is heated at 180° C. under an inert atmosphere for 2.5 hours.

The reaction mixture is cooled to ambient conditions and 600 ml HCl is added to the mixture which is stirred for 15 min. The pH of the mixture is adjusted to pH 3. Next, 200 ml of water is added into the mixture and stirred for 5 min. The mixture is transferred into a 4 L separatory funnel and extracted three times with 500-ml portions of hexane.

The aqueous layer is drained and the combined hexane solution extracted with four 250-ml portions of 5% NaCl solution.

The hexane is washed 3 times with water. The hexane is transferred to a flask and the moisture in the hexane removed with anhydrous sodium sulfate ($Na_2SO_4$). The hexane is filtered through Whatman paper into a clean 1000 ml round bottom flask and the hexane removed under vacuum with a rotoevaporator to obtain the CLA. The CLA is stored in a dark bottle under argon at −80° C. until time of use.

EXAMPLE 2

Twenty-four White Leghorn hens were divided into 2 groups. Each bird was housed in an individual pen and provided with water and fed ad libitium for the experiment. The birds were maintained for an adaptation period of a week on a basal corn/soy diet, then were fed with either the control diet, or a 0.5% CLA supplemented diet. Following 4 weeks of the experimental period, hens were fertilized, eggs were collected for 3 days at the end of each week over a period of 4 weeks. It was then noted that the eggs of the hens fed the CLA failed to hatch live chicks. While the experiment was being conducted, it was noted that the egg yolk became hard when refrigerated. To explain this physical change, a fatty acid analysis was conducted. The composition of total saturated fatty acid (SFA) increased, while total unsaturated fatty acid decreased in the CLA group. This difference was notably significant (see Table 1 below).

TABLE 1

EFFECT OF CLA ON FATTY ACID COMPOSITION OF EGG YOLK LIPIDS

| Fatty acid | Control % of Total Fatty Acids | CLA (Mean ± SE) | p< |
| --- | --- | --- | --- |
| C12:0 | 0.012 ± 0.003 | 0.015 ± 0.001 | NS |
| C14:0 | 0.400 ± 0.011 | 0.665 ± 0.024 | <0.0001 |
| C16:0 | 27.470 ± 0.258 | 34.771 ± 0.255 | <0.0001 |

TABLE 1-continued

EFFECT OF CLA ON FATTY ACID COMPOSITION OF EGG YOLK LIPIDS

| Fatty acid | Control % of Total Fatty Acids | CLA (Mean ± SE) | p< |
| --- | --- | --- | --- |
| C16:1 | 2.516 ± 0.076 | 1.308 ± 0.033 | <0.0001 |
| C18:0 | 10.779 ± 0.131 | 20.194 ± 0.198 | <0.0001 |
| C18:1 | 41.254 ± 0.358 | 24.249 ± 0.270 | <0.0001 |
| C18:2 | 14.953 ± 0.338 | 14.577 ± 0.178 | NS |
| C18:3 | 0.287 ± 0.010 | 0.343 ± 0.013 | 0.003 |
| C20:4 | 2.262 + 0.077 | 1.811 ± 0.045 | <0.0001 |
| CLA | 0.075 ± 0.002 | 10.998 + 0.058 | <0.0001 |
| % total SFA | 38.661 | 55.645 | |
| % total MUFA | 43.770 | 25.557 | |
| % total PUFA | 17.577 | 18.799 | |

NS = non-significant; SFA = Saturated Fatty Acids; MUFA = monounsaturated fatty acids; and, PUFA = polyunsaturated acids.

EXAMPLE 3

Baits for use in the method of the present invention are made containing 0.5% by weight of a mixture of conjugated linoleic acids (CLA) in food or a non-toxic biopolymer. The mixture is ground and extruded to provide bait particles of the following particle size:

| Size of Bait Particles | Targeted Species |
| --- | --- |
| 12 to 16 cm × 2 to 3 cm (smelt size) | Seagulls |
| 0.5 cm × 0.5 cm (popcorn size) | Pigeons |
| 2.5 cm × 1 cm | Blackbirds and Crows |
| 2.5 cm × 1 cm | Starlings |
| 0.4 cm × 0.4 cm | House Sparrows |

EXAMPLE 4

The seagull population of an airport is controlled by feeding to the gulls at the islands where they breed during the nesting season a bait containing CLA and having a particle size of about 12 cm long and about 3 cm in diameter.

In addition to the use of baits containing CLA in a biopolymer, baits can be used which simply comprise a normal feed for the targeted birds to which the CLA has been added, preferably by coating the feed.

The active forms of CLA include, in addition to the free acids the active isomers of CLA; non-toxic salts thereof; active esters and other active chemical derivatives thereof; and mixtures thereof.

The free conjugated linoleic acids (CLA) have been previously isolated from fried meats and described as anti-carcinogens by Y. L. Ha, N. K. Grimm and M. W. Pariza, in Carcinogenesis Vol. 8, No. 12, pp. 1881–1887 (1987). Since then, they have been found in some processed cheese products. Y. L. Ha, N. K. Grimm and M. W. Pariza, in J. Agric. Food Chem., Vol. 37, No. 1, pp. 75–81 (1987).

The free acid forms of the CLA may be prepared by isomerizing linoleic acid. The terms "conjugated linoleic acids" and "CLA" as used herein are intended to include 9,11-octadecadienoic acid, 10,12-octadecadienoic acid, mixtures thereof, and the non-toxic salts of the acids. The non-toxic salts of the free CLA acids may be made by reacting the free acids with a non-toxic base.

The preferred method of synthesizing CLA is that described in Example 1. However, CLA may also be prepared from linoleic acid by the action of a linoleic acid isomerase from a harmless microorganism, such as the Rumen bacterium *Butyrivibrio fibrisolvens*. Harmless microorganisms in the intestinal tracts of rats and other monogastric animals may also convert linoleic acid to CLA. S. F. Chin, J. M. Storkson, W. Liu, K. Albright and M. W. Pariza, 1994, J. Nutr. 124:694–701.

The CLA obtained by the practice of the described methods of preparation contains one or more of the 9,11-octadecadienoic acids and/or 10,12-octadecadienoic acids and active isomers thereof. It may be free or bound chemically through ester linkages. The CLA is heat stable and can be used as is, or dried and powdered. The CLA is readily converted into a non-toxic salt, such as the sodium or potassium salt, by reacting chemically equivalent amounts of the free acid with an alkali hydroxide at a pH of about 8 to 9.

Theoretically, 8 possible geometric isomers of 9,11-and 10,12-octadecadienoic acid (c9,c11; c9,t11; t9,c11; t9,t11; c10,c12; c10,t12; t10,c12 and t10,t12) would form from the isomerization of c9,c12-octadecadienoic acid. As a result of the isomerization, only four isomers (c9,c11; c9,t11; t10, c12; and c10,c12) would be expected. However, of the four isomers, c9,t11- and t10,c12- isomers are predominantly produced during the autoxidation or alkali-isomerization of c9,c12-linoleic acid due to the co-planar characteristics of 5 carbon atoms around a conjugated double-bond and spatial conflict of the resonance radical. The remaining two c,c-isomers are minor contributors.

The relatively higher distribution of the t,t-isomers of 9,11- or 10,12-octadecadienoic acid apparently results from the further stabilization of c9,t11- or t10,c12geometric isomers, which is thermodynamically preferred, during an extended processing time or long aging period. Additionally the t,t-isomer of 9,11- or 10,12-octadecadienoic acid that was predominantly formed during the isomerization of linoleic acid geometrical isomers (t9,t12-, c9,t12- and t9,c12-octadecadienoic acid) may influence the final ratio of the isomers or the final CLA content in the samples.

Linoleic acid geometrical isomers also influence the distribution of minor contributors (c,c-isomers of 9,11- and 10,12-, t9,c11- and c11,t12-octadecadienoic acids). The 11,13-isomer might be produced as a minor product from c9,c12-octadecadienoic acid or from its isomeric forms during processing.

It will be readily apparent to those skilled in the art that a number of modifications or changes may be made without departing from the spirit and scope of the present invention. Therefore, the invention is only to be limited by the claims.

We claim:

1. A method of controlling bird populations by preventing eggs from hatching, said method comprising administering to the female birds of said population an amount of conjugated linoleic acid which is effective to prevent the eggs of said birds from hatching.

2. A method of claim 1 in which the birds are seagulls.

3. A method of claim 1 in which the birds are pigeons.

4. A method of claim 1 in which the birds are blackbirds.

5. A method of claim 1 in which the birds are starlings.

6. A method of claim 1 in which the birds are crows.

7. A method of claim 1 in which the birds are sparrows.

8. A method of claim 1 in which the birds are waterfowl.

9. A method of claim 1 in which the conjugated linoleic acid is contained in a feed which is of a particle size preferred by the birds.

10. A method of reducing bird populations in an area by preventing eggs from hatching, which comprises administering to at least some of the female birds in that area an amount of conjugated linoleic acid which is effective to prevent the eggs produced by said female birds from hatching.

* * * * *